United States Patent [19]
Van Ooijen

[11] Patent Number: 5,371,287
[45] Date of Patent: Dec. 6, 1994

[54] RELEASABLY BOUND HYDROXYCARBOXYLIC ACIDS

[75] Inventor: Johannes A. C. Van Ooijen, Giessenburg, Netherlands

[73] Assignee: BP Chemicals Limited, London, England

[21] Appl. No.: 179,931

[22] Filed: Jan. 11, 1994

[30] Foreign Application Priority Data

Jan. 27, 1993 [GB] United Kingdom ............. 9301532.9

[51] Int. Cl.$^5$ ............................................. C07L 59/08
[52] U.S. Cl. ................................... 562/589; 562/582; 562/587
[58] Field of Search ...................... 562/589, 582, 587

[56] References Cited

U.S. PATENT DOCUMENTS

| | | | |
|---|---|---|---|
| 2,557,283 | 6/1951 | Hansen | 562/589 |
| 3,060,096 | 10/1962 | Wei | 562/587 |
| 4,282,385 | 4/1981 | Metz | 562/589 |

FOREIGN PATENT DOCUMENTS 0590856  4/1994  European Pat. Off. .

*Primary Examiner*—Paul J. Killos
*Attorney, Agent, or Firm*—Brooks Haidt Haffner & Delahunty

[57] ABSTRACT

This invention relates to a composition which has an alkali(ne earth) metal hydroxycarboxylate and an aliphatic carboxylic acid which has a lower pKa than that of the hydroxycarboxylic acid. The hydroxycarboxylate salt, when used e.g. in an aqueous medium which allows dissociation of the salt and the aliphatic carboxylic acid into anions and cations, dissociates into the metal ions and hydroxycarboxylate ions, and the acid into the corresponding carboxylate ions and hydrogen ions. The relative pKa values of the two acids ensure that the aliphatic acid forms the alkali(ne earth metal salt thereby liberating the free hydroxycarboxylic acid in situ. This method masks the unpleasant odors of acids for ensiling etc without causing distress to operatives during storage and use.

9 Claims, No Drawings

RELEASABLY BOUND HYDROXYCARBOXYLIC ACIDS

The invention relates to a method of storing and using hydroxycarboxylic acids, especially lactic acid, releasably, bound on a support.

It is well known that one of the most common hydroxycarboxylic acids is lactic acid. This acid has a melting point of 26° C. in its purest form but is usually a hygroscopic and syrupy liquid under ambient conditions due to the inevitable presence of water and minor impurities therein when produced on a commercial scale. Similar problems occur with gluconic acids (pKa 3.7). The hygroscopic and syrupy nature of such compounds presents significant difficulties during storage and transportation. In fact, hydroxyacids such as lactic acid also present corrosion problems. Yet this acid has a number of commercial uses in various industries such as e.g. baking, confectionery, sauce-making, meat/meat products, beer, wine and cider, soft drinks and fruit juices, salads, mayonnaise and dressings, pickles, marinades, pharmaceuticals e.g. infusion solutions, dialysis solutions and cephalosporin antibiotics, cosmetics, surface treatment of metals, metal plating, leather, synthetic resins, printing inks and to a lesser extent as an animal feed supplement. Thus, the industry would like to store and transport this or similar acids in a readily hanbdleable form e.g. a powder provided that such powder can be readily converted to the acid at the point of use without any adverse effect on the formulations where such acids are used.

It has now been found that these problems can be mitigated by storing such hydroxy carboxylic acids in the form of their alkali(ne earth) metal salt either as such or admixed with another carboxylic acid of defined physical properties such that the free hydroxycarboxylic acid is released at the point of use when such admixture is brought into contact with an appropriate solvent system.

Accordingly, the present invention is a composition comprising an alkali(ne earth) metal carboxylate of a hydroxycarboxylic acid which is a liquid or a semi-solid at ambient temperature, and an aliphatic carboxylic acid which has a lower pKa than that of the hydroxycarboxylic acid.

The hydroxycarboxylic acid may be a mono-, di- or poly-hydroxycarboxylic acid. The present technique is particularly suitable for hydroxycarboxylic acids such as lactic acid (pKa 3.08) and gluconic acid (pKa 3.7).

A feature of the invention is that the alkali(ne earth) carboxylate of the hydroxy carboxylic acid, when used in a medium capable of allowing dissociation of the salt or free carboxylic acids into anions and cations e.g. in aqueous systems, dissociates into the alkali(ne earth) metal ions and hydroxycarboxylate ions, and the aliphatic carboxylic acid in turn dissociates into the corresponding carboxylate ion and hydrogen ions. However, due to the relative differences in the pKa values (i.e. dissociation constants), the aliphatic carboxylate ion combines preferentially with the alkali(ne earth) metal ions to form the alkali(ne earth) metal salt of the aliphatic carboxylic acid and releases the free hydroxycarboxylic acid in situ.

The hydroxycarboxylic acids which can benefit by this technique suitably include acids which contain a hydroxy group(s) either alone or in combination with other functional groups such as e.g. amino groups. Specific examples of such carboxylic acids are lactic acid (pKa 3.08) and gluconic acid (pKa 3.7)which are the most suited to this technique due to their syrupy and hygroscopic nature.

The process works particularly efficiently if the alkali(ne earth) metal salt of the aliphatic carboxylic acid so formed readily soluble in the solvent system used to generate the hydroxycarboxylic acid. However, for practical reasons, it may be preferable, though not essential, to form a substantially insoluble alkali(ne earth) metal salt in order to enable easy separation of the hydroxycarboxylic acid solution from the insoluble salt by decantation or filtration immediately prior to use. Such an insoluble salt can be formed by the appropriate selection of reactants and/or solvents. It should be noted, however, that in the process of separating the hydroxycarboxylic acid solution from the precipitate, some of the yield of available hydroxycarboxylic acid may be lost due to occlusion on the precipitate.

Particularly suitable alkali(ne earth) metal salts for use in the compositions of the present invention are those of sodium, potassium, calcium and magnesium.

The aliphatic carboxylic acids which have a pKa value lower than that of the functionalised carboxylic acid under comparable conditions would be suitable for admixing with the alkali(ne earth) metal hydroxycarboxylate. Such aliphatic carboxylic acids may be mono-, di- or poly-carboxylic acids and may be saturated or unsaturated. Particularly suitable for this purpose are the di- and poly-carboxylic acids, especially the unsaturated carboxylic acids due to their ability to form alkaline earth metal salts which have very low solubility in aqueous systems, e.g. water. Specific examples of the preferred aliphatic carboxylic acids include trans-fumaric acid (pKa 3.03), maleic acid (pKa 1.83), malonic acid (pKa 2.83) and methyl-malonic acid (pKa 3.07).

For instance, if fumaric acid, which has substantially low volatility, is intimately mixed with a calcium lactate salt and stored as such, the problems of instability and volatility are immediately alleviated. However, when the fumaric acid admixed with the calcium lactate is brought into contact with a suitable solvent, e.g. water, at the point of use and at room temperature, a rapid exchange takes place and the lactic acid is liberated immediately into the aqueous solution in situ leaving behind a substantially insoluble precipitate of calcium fumarate which can, if so desired, be readily removed by filtration or decantation.

The aqueous solution containing lactic acid and some calcium fumarate can then be used as desired.

The above reaction can be represented as follows:

The alkali(ne earth) metal hydroxycarboxylate and the aliphatic carboxylic acid in the composition may be combined together in various ways. For instance, if the aliphatic carboxylic is a solid, this can be intimately mixed with the calcium salt of the hydroxycarboxylic acid and form a solid mixture. However, if the aliphatic carboxylic acid is a liquid, this liquid can be used to impregnate the solid calcium carboxylate of the hydroxycarboxylic acid. The admixed or impregnated calcium salt of the hydroxycarboxylic acid can then be stored and used as desired.

The amount of aliphatic carboxylic acid present in the composition along with the alkali(ne earth) metal salt of the hydroxycarboxylic acid is limited only by the physical ability of the two to be admixed or for the former to be impregnated on the latter. The hydroxycarboxylate salt may, for instance, be admixed or impregnated with 1 to 90% w/w, preferably 40–60% w/w of the aliphatic carboxylic acid based on the total weight of the alkali(ne earth) metal salt of the hydroxycarboxylic acid. An equimolar mixture of the aliphatic carboxylic acid and the hydroxycarboxylate salt is most preferred.

Each of the alkali(ne earth) metal hydroxycarboxylate and the aliphatic carboxylic acid admixed therewith may be, if not a liquid, in the form of a powder or granules, or can be shaped into any other convenient shape or form, e.g. pellets. The physical shape of the two will be determined by the desired speed of release of the hydroxycarboxylic acid once they are in contact with the appropriate solvent system. It would be clear that for a slow release system, the admixture of the two will be highly compacted.

Whichever form of the components is used in the composition, it will be clear that in order for the hydrocarboxylic acid to be released from the salt, the admixture has to be brought into contact with an aqueous or non-aqueous system, e.g. water, which is capable of allowing the salt and the carboxylic acid to dissociate in said system. Upon intimately mixing the alkali(ne earth) metal hydroxycarboxylate and the aliphatic carboxylic acid with the solvent system, the exchange of ions takes place.

Thus according to a further embodiment, the present invention is a method of releasing a hydroxycarboxylic acid in situ in a solvent system capable of allowing a salt of the hydroxycarboxylic acid and an aliphatic carboxylic acid of lower pKa value than the hydroxycarboxylic acid to ionize in said system, said method comprising bringing into contact with the solvent system an alkali(ne earth) metal salt of the hydroxycarboxylic acid and the aliphatic carboxylic acid whereby a solution comprising the free hydroxy carboxylic acid in the solvent is generated.

The following Examples will, for the sake of convenience, be directed to an admixture of an aqueous solution of calcium lactate with fumaric acid with a view to generating lactic acid in situ, but should in no way be construed as limiting the generic inventive concept disclosed herein.

EXAMPLE

A mixture of calcium lactate (6.7 g, 1 mol water) and fumaric acid (3.3 g) was dissolved in 100 ml of water to form a solution. The solution was then stirred for one hour and filtered through a Whatman glass microfibre filter. The free acid content of the filtrate was measured by titrating against a 0.1N aqueous sodium hydroxide solution. The free acid content of the filtrate was assumed to be that contributed by lactic acid alone since fumaric acid is not soluble in water. The experiment was repeated twice. The efficiency of conversion of calcium lactate to free lactic acid in situ in these experiments was calculated on this basis to be about 94% as follows:

The measured amounts of free acid in the mixtures from the two experiments were 4.33 and 4.42%. After stirring, the mixtures were almost clear, so the total weight of the mixture was $$100+6.7+3.3=110 \text{ g}$$

(no loss of weight was observed during filtration). The actual amounts of lactic acid that could be detected by titration in 110 g were 4.76 g and 4.86 g respectively corresponding to the yield of 4.33 and 4.42% respectively. The maximum amount of lactic acid that could be present, based on calcium lactate (6.7 g, 1 mol water of crystallization) intake, is 5.11 g. Therefore, the efficiency of the conversion was:

$$(4.76+4.86)\times 100/(2\times 5.11)\% = (4.81\times 100)/5.11\% = 94.1\%$$

The above experiments show that lactic acid can be generated efficiently in situ from a salt thereof admixed with fumaric acid in an aqueous solution.

I claim:

1. A composition comprising an alkali(ne earth) metal carboxylate of a hydroxycarboxylic acid which is a liquid or a semi-solid at ambient temperature, and an aliphatic carboxylic acid which has a lower pKa than that of the hydroxycarboxylic acid.

2. A composition according to claim 1 said composition comprising
   a. an alkali(ne earth) metal carboxylate of a hydroxycarboxylic acid which is a liquid or a semi-solid at ambient temperature,
   b. an aliphatic carboxylic acid which has a lower pKa than that of the hydroxycarboxylic acid, and
   c. a solvent system capable of allowing ionisation of the alkali(he earth) metal salt of the hydroxycarboxylic acid and the aliphatic carboxylic acid such that when components (a), (b) and (c) are brought together, free hydroxycarboxylic acid is released in situ into the solvent system.

3. A composition according to claim 1 wherein the hydroxycarboxylic acid is a mono-, di- or poly-hydroxycarboxylic acid.

4. A composition according to claim 1 wherein the hydroxycarboxylic acid is lactic acid or gluconic acid.

5. A composition according to claim 1 wherein the aliphatic carboxylic acid having a pKa lower than that of the hydrocarboxylic acid in said composition is selected from the group consisting of mono-, di- and poly-carboxylic acids which may be saturated or unsaturated.

6. A composition according to claim 1 wherein the aliphatic carboxylic acid having a pKa lower than that of the hydroxycarboxylic acid in said composition is selected from the group consisting of trans-fumaric acid, maleic acid, malonic acid and methyl-malonic acid.

7. A composition according to claim 1 wherein the amount of aliphatic carboxylic acid having a lower pKa value than that of the hydroxycarboxylic acid present in the composition with respect to the alkali(ne earth) metal salt of the hydroxycarboxylic acid is in the range from 1 to 90% by weight.

8. A composition according to claim 1 wherein each of the alkali(ne earth) metal salt of the hydroxycarboxylic acid and the aliphatic carboxylic acid having a lower pKa value than the hydroxycarboxylic acid in the composition is in a form which is the same or different and is selected from the group consisting of liquid, solution, powder, granules or shaped pellets.

9. A method of releasing free hydroxycarboxylic acids in situ in a solvent system capable of allowing the alkali(ne earth) metal salt thereof and an aliphatic carboxylic acid having a lower pKa value than that of the hydroxycarboxylic acid to ionise in said system, said method comprising bringing into contact with the solvent system a composition comprising said alkali(ne earth) metal salt of the hydroxycarboxylic acid and the aliphatic carboxylic acid according to claim 1, thereby generating a solution comprising the free hydroxycarboxylic acid in said solvent system.

* * * * *

UNITED STATES PATENT AND TRADEMARK OFFICE
CERTIFICATE OF CORRECTION

PATENT NO. : 5,371,287
DATED : December 6, 1994
INVENTOR(S) : JOHANNES A.C. VAN OOIJEN It is certified that error appears in the above-indentified patent and that said Letters Patent is hereby corrected as shown below:

Title page, item [57], col. 2,

In the Abstract, line 11, after "earth" insert a closed parenthesis.

Col. 1, l. 7, delete the comma (,) after "releasably".

Col. 2, l. 7, after "formed" and before "readily" insert --is--.

Col. 2, l. 15, change "reactants" to --reagents--.

Signed and Sealed this

Fourteenth Day of February, 1995

Attest:

BRUCE LEHMAN

Attesting Officer     Commissioner of Patents and Trademarks